(12) United States Patent
Kakinuma et al.

(10) Patent No.: US 10,399,930 B2
(45) Date of Patent: Sep. 3, 2019

(54) PURIFICATION METHOD OF ALDEHYDE COMPOUND

(71) Applicant: Mitsui Chemicals, Inc., Minato-ku, Tokyo (JP)

(72) Inventors: Naoyuki Kakinuma, Omuta (JP);
Masayuki Furuya, Arao (JP);
Michiharu Sakata, Kurume (JP);
Koichi Tokunaga, Chikugo (JP);
Shigetoshi Kuma, Kurume (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 15/723,778

(22) Filed: Oct. 3, 2017

(65) Prior Publication Data

US 2018/0093945 A1    Apr. 5, 2018

Related U.S. Application Data

(62) Division of application No. 14/434,114, filed as application No. PCT/JP2013/080315 on Nov. 8, 2013, now Pat. No. 9,809,533.

(30) Foreign Application Priority Data

Nov. 9, 2012  (JP) ................... 2012-247464

(51) Int. Cl.
| | |
|---|---|
| C07C 265/14 | (2006.01) |
| C07C 263/10 | (2006.01) |
| C07C 255/47 | (2006.01) |
| B01J 31/24 | (2006.01) |
| C07C 211/19 | (2006.01) |
| C07B 63/00 | (2006.01) |
| C07C 209/26 | (2006.01) |
| C07C 253/30 | (2006.01) |
| C07C 253/34 | (2006.01) |

(52) U.S. Cl.
CPC ............ *C07C 263/10* (2013.01); *B01J 31/24* (2013.01); *C07B 63/00* (2013.01); *C07C 209/26* (2013.01); *C07C 211/19* (2013.01); *C07C 253/30* (2013.01); *C07C 253/34* (2013.01); *C07C 255/47* (2013.01); *C07C 265/14* (2013.01); *C07C 2602/42* (2017.05)

(58) Field of Classification Search
CPC .... C07C 265/14; C07C 263/10; C07C 255/47
See application file for complete search history.

(56) References Cited

U.S. PATENT DOCUMENTS

| | | |
|---|---|---|
| 3,143,570 A | 8/1964 | Caldwell et al. |
| 4,649,214 A | 3/1987 | Gladfelter et al. |
| 5,307,024 A | 4/1994 | Metz et al. |
| 5,312,951 A | 5/1994 | Herrmann et al. |
| 6,252,121 B1 | 6/2001 | Argyropoulos et al. |
| 9,227,925 B2 | 1/2016 | Kuma et al. |

FOREIGN PATENT DOCUMENTS

| | | |
|---|---|---|
| EP | 0065294 A1 | 11/1982 |
| EP | 2708527 A1 | 3/2014 |
| JP | 57-193438 A | 11/1982 |
| JP | 60-72844 A | 4/1985 |
| JP | H03-220167 A | 9/1991 |

(Continued)

OTHER PUBLICATIONS

Franke et al, 2012, Chemical Reviews, vol. 112, p. 5675-5732. (Year: 2012).*
English machine translation of JP H03-220167, p. 1-11. (Year: 1991).*
International Search Report (PCT/ISA/210) dated Feb. 4, 2014, by the Japanese Patent Office as the International Searching Authority for International Application No. PCT/JP2013/080315.

(Continued)

*Primary Examiner* — Karen Cheng
(74) *Attorney, Agent, or Firm* — Buchanan, Ingersoll & Rooney PC

(57) ABSTRACT

A manufacturing method of an isocyanate compound including obtaining a reaction solution containing an aldehyde compound by reacting a compound represented by Formula (a1) or (a2) with hydrogen and carbon monoxide in the presence of a metal compound of groups 8 to 10 and a phosphorus compound, neutralizing the reaction solution, purifying an aldehyde compound by distilling the neutralized reaction solution, reacting the aldehyde compound with ammonia and with hydrogen in the presence of a catalyst to obtain an amine compound; and reacting the amine compound with a carbonylating agent to obtain an isocyanate compound, wherein the phosphorus compound is represented by the Formula $(R^1O)_3P$, and the base compound is at least one selected from carbonate and hydrogen carbonate of metals of group I and carbonate and hydrogen carbonate of metals of group II,

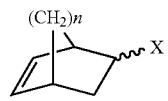
(a1)

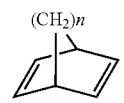

(a2)

wherein the neutralizing the reaction solution is performed within a temperature range of 40° C. to 50° C.

5 Claims, 3 Drawing Sheets

(56) References Cited

FOREIGN PATENT DOCUMENTS

| JP | 6-49554 A | 2/1994 |
|----|-----------|--------|
| JP | 6-87876 A | 3/1994 |
| JP | 2001-261660 A | 9/2001 |
| JP | 2003-505438 A | 2/2003 |
| JP | 2007-320944 A | 12/2007 |
| KR | 2002-0039324 A | 5/2002 |
| WO | WO 93/03839 A1 | 3/1993 |
| WO | WO 2012/153509 A1 | 11/2012 |

OTHER PUBLICATIONS

Hayashi et al., "Preparation of alicyclic-aliphatic diisocyanates", Database CA [Online]; Chemical Abstracts Service, Columbia, Ohio, US, XO002757834, Database accession No. 1992:105699.

Extended Search Report issued by the European Patent Office in corresponding European Patent Application No. 13853532.3 dated May 30, 2016 (12 pages).

Tafesh et al., "A Review of the Selective Reduction of Aromatic Nitro Compounds into Aromatic Amines, Isocyanates, Carbamates, and Ureas Using CO'", Chem. Rev. vol. 96, pp. 2035-2052.

Office Action issued by the Korean Patent Office in corresponding Korean Patent Application No. 10-2015-7008055 dated Sep. 12, 2016 (16 pages with partial English translation).

English machine translation of JP 60-072844, Yoshio et al., pub. Apr. 24, 1985, pp. 1-11.

English machine translation of JP 60-49554, pub. Feb. 22, 1994, pp. 1-12.

\* cited by examiner

PURIFICATION METHOD OF ALDEHYDE COMPOUND

CROSS-REFERENCE TO RELATED APPLICATIONS

This application is a divisional of U.S. application Ser. No. 14/434,114, filed Apr. 8, 2015, which is a U.S. National Stage Application of PCT/JP2013/080315, filed Nov. 8, 2013, which claims priority to Japanese Patent Application No. 2012-247464, filed Nov. 9, 2012, the contents of all of which are hereby incorporated by reference.

TECHNICAL FIELD

The present invention relates to a purification method of a aldehyde compound, a manufacturing method of an aldehyde compound including the purification method as a step, and a manufacturing method of an amine compound and a manufacturing method of an isocyanate compound that use an aldehyde compound obtained by the aforementioned manufacturing method.

BACKGROUND ART

As a manufacturing method of an aldehyde compound using a norbornene compound, for example, the methods described in Patent Documents 1 to 3 are known.

Patent Documents 1 to 3 disclose methods for manufacturing formyl cyan norbornane by hydroformylating cyan norbornene by using a mixed gas of $H_2$/CO in the presence of a catalyst. Patent Documents 1 and 2 disclose an example in which a metal compound is used as a catalyst. Herein, because a target compound can be obtained with a high degree of selectivity, and a reaction pressure can be kept low, a rhodium complex is preferably used as a catalyst.

Patent Document 4 describes a metal ligand complex catalyst. In this document, rhodium is exemplified as a metal, and an organic phosphorus ligand is exemplified as a ligand.

Patent Document 5 discloses a method for treating a solution, which contains a trivalent phosphorus compound, a rhodium compound, and an aldehyde compound, that is for recovering the rhodium metal. In the document, hydrolysis using water and a base compound such as NaOH is used.

RELATED DOCUMENT

Patent Document

[Patent Document 1] Japanese Laid-open Patent Publication No. 57-193438
[Patent Document 2] Japanese Laid-open Patent Publication No. 60-72844
[Patent Document 3] U.S. Pat. No. 3,143,570
[Patent Document 4] Japanese Translation of PCT International Application No. 2003-505438
[Patent Document 5] Japanese Laid-open Patent Publication No. 6-49554

DISCLOSURE OF THE INVENTION

The present inventors found that when an amine compound is synthesized by imino-hydrogenating an aldehyde compound, if a compound derived from a phosphorus compound used for a hydroformylation reaction remains, yield of the reaction is reduced. In order to improve the yield of the reaction, after the hydroformylation reaction, the obtained aldehyde compound and the compound derived from the phosphorus compound need to be separated beforehand.

However, when the boiling point of the aldehyde compound is close to the boiling point of the compound derived from the phosphorus compound, it is difficult to separate the compounds by distillation in some cases. Furthermore, when the phosphorus compound is hydrolyzed such that it can be separated by distillation, the solution becomes acidic, and thus the aldehyde compound loses stability in some cases. In addition, when the acidic solution obtained after the hydrolysis is neutralized with a base compound so as to improve the stability of the aldehyde compound, the base compound causes polymerization/decomposition of the aldehyde compound, and thus the stability deteriorates in some cases.

For this reason, the present invention aims to establish a purification technique of an aldehyde compound that separates an aldehyde compound and a compound derived from a phosphorus compound while maintaining stability of the aldehyde compound as a target substance.

As a result of performing intensive examination to solve the above problem, the present inventors found a method for separating a compound derived from a phosphorus compound while maintaining stability of an aldehyde compound by using a predetermined base compound.

The present invention includes the following.

[1] A purification method of an aldehyde compound, including a step of neutralizing a reaction solution containing an aldehyde compound by adding water and a base compound to the reaction solution, and a step of distilling the neutralized reaction solution, in which the reaction solution is obtained by reacting a compound represented by the following Formula (a1) or (a2) with hydrogen and carbon monoxide in the presence of a metal compound of groups 8 to 10 and a phosphorus compound, the phosphorus compound is represented by the following Formula $(R^1O)_3P$, and the base compound is at least one kind selected from among carbonate and hydrogen carbonate of metals of group I on the periodic table and carbonate and hydrogen carbonate of metals of group II on the periodic table,

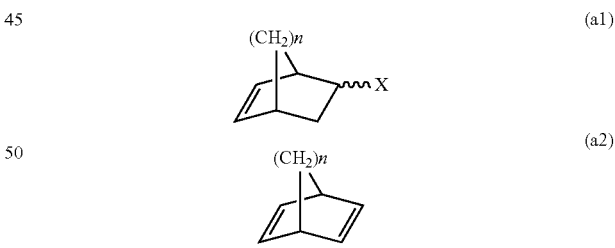

(in Formula (a1), X represents a hydrogen atom, a cyano group, an aldehyde group, or a —CH=NR group; R represents a hydrogen atom, an alkyl group having 1 to 6 carbon atoms, or an aryl group; and in Formulae (a1) and (a2), n represents 0, 1, or 2), $(R^1O)_3P$ (in the formula, a plurality of $R^1$s may be the same as or different from each other, and represents an alkyl group having 1 to 16 carbon atoms that may have a substituent or an aryl group having 6 to 16 carbon atoms that may have a substituent).

[2] The purification method of an aldehyde compound described in [1], in which the base compound is potassium hydrogen carbonate or potassium carbonate.

[3] The purification method of an aldehyde compound descried in [1] or [2], in which the phosphorus compound is at least one kind selected from the group consisting of triphenyl phosphite, trimethyl phosphite, triethyl phosphite, tripropyl phosphite, triisopropyl phosphite, trimethylphenyl phosphite, and tris(2,4-di-tert-butylphenyl)phosphite.

[4] The purification method of an aldehyde compound described in any one of [1] to [3], in which the metal compound of groups 8 to 10 is a rhodium compound, a cobalt compound, a ruthenium compound, or an iron compound.

[5] The purification method of an aldehyde compound described in any one of [1] to [3], in which the metal compound of groups 8 to 10 is a rhodium compound.

[6] The purification method of an aldehyde compound described in any one of [1] to [5], in which a compound represented by the Formula (a1) is used, and the compound is a compound represented by the following Formula (1),

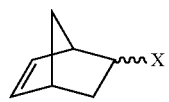

(1)

(in Formula (1), X has the same definition as X in Formula (a1)).

[7] The purification method of an aldehyde compound described in any one of [1] to [6], in which the step of neutralizing the reaction solution is performed within a temperature range of equal to or higher than 40° C. and equal to or lower than 50° C.

[8] A manufacturing method of an aldehyde compound, including a step of obtaining a reaction solution containing an aldehyde compound by reacting a compound represented by the following Formula (a1) or (a2) with hydrogen and carbon monoxide in the presence of a metal compound of groups 8 to 10 and a phosphorus compound, a step of neutralizing the reaction solution by adding water and a base compound to the reaction solution, and a step of purifying an aldehyde compound by distilling the neutralized reaction solution, in which the phosphorus compound is represented by the following Formula $(R^1O)_3P$, and the base compound is at least one kind selected from among carbonate and hydrogen carbonate of metals of group I on the periodic table and carbonate and hydrogen carbonate of metals of group II on the periodic table,

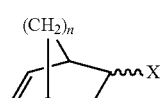

(a1)

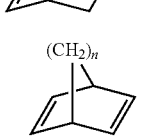

(a2)

(in Formula (a1), X represents a hydrogen atom, a cyano group, an aldehyde group, or a —CH═NR group; R represents a hydrogen atom, an alkyl group having 1 to 6 carbon atoms, or an aryl group; and in Formulae (a1) and (a2), n represents 0, 1, or 2), $(R^1O)_3P$ (in the formula, a plurality of $R^1$s may be the same as or different from each other, and represents an alkyl group having 1 to 16 carbon atoms that may have a substituent or an aryl group having 6 to 16 carbon atoms that may have a substituent).

[9] The manufacturing method of an aldehyde compound described in [8], in which the base compound is potassium hydrogen carbonate or potassium carbonate.

[10] The manufacturing method of an aldehyde compound described in [8] or [9], in which the phosphorus compound is at least one kind selected from the group consisting of triphenyl phosphite, trimethyl phosphite, triethyl phosphite, tripropyl phosphite, triisopropyl phosphite, trimethylphenyl phosphite, and tris(2,4-di-tert-butylphenyl) phosphite.

[11] The manufacturing method of an aldehyde compound described in any one of [8] to [10], in which the metal compound of groups 8 to 10 is a rhodium compound, a cobalt compound, a ruthenium compound, or an iron compound.

[12] The manufacturing method of an aldehyde compound described in any one of [8] to [10], in which the metal compound of groups 8 to 10 is a rhodium compound.

[13] The manufacturing method of an aldehyde compound described in any one of [8] to [12], in which a compound represented by the Formula (a1) is used, and the compound is a compound represented by the following Formula (1),

(1)

(in Formula (1), X has the same definition as X in Formula (a1)).

[14] The manufacturing method of an aldehyde compound described in any one of [8] to [13], in which the step of neutralizing the reaction solution is performed within a temperature range of equal to or higher than 40° C. and equal to or lower than 50° C.

[15] A manufacturing method of an amine compound, including a step of reacting an aldehyde compound obtained by the manufacturing method described in any one of [8] to [14] with ammonia and with hydrogen in the presence of a catalyst.

[16] A manufacturing method of an isocyanate compound, including a step of reacting an amine compound obtained by the manufacturing method described in [15] with a carbonylating agent.

In the present invention, a "phosphorus compound" refers to a phosphorus compound that can form a complex with a metal compound, and includes any of a phosphorus compound having formed a complex with a metal compound and a free phosphorus compound.

Furthermore, in the present invention, when a substance B is used in an amount of $1 \times 10^{-6}$ mol with respect to 1 mol of a substance A, the amount of the substance B is described as 1 ppmmol.

Effect of the Invention

According to the purification method of an aldehyde compound of the present invention, it is possible to separate a compound derived from a phosphorus compound while maintaining stability of an aldehyde compound. Consequentially, it is possible to obtain an aldehyde compound, from which the compound derived from the phosphorus compound has been separated and removed, while maintaining the yield.

The manufacturing method of an aldehyde compound, the manufacturing method of an amine compound, and the manufacturing method of an isocyanate compound using the amine compound obtained by the aforementioned manufacturing method of the present invention include the purification method of an aldehyde compound as a step. Accordingly, the manufacturing methods are excellent in productivity and yield of the target compounds.

BRIEF DESCRIPTION OF THE DRAWINGS

The aforementioned object, other objects, characteristics, and advantages become clearer by preferable embodiments described below and the following drawings accompanied by the embodiments.

DESCRIPTION OF EMBODIMENTS

Figure 1:
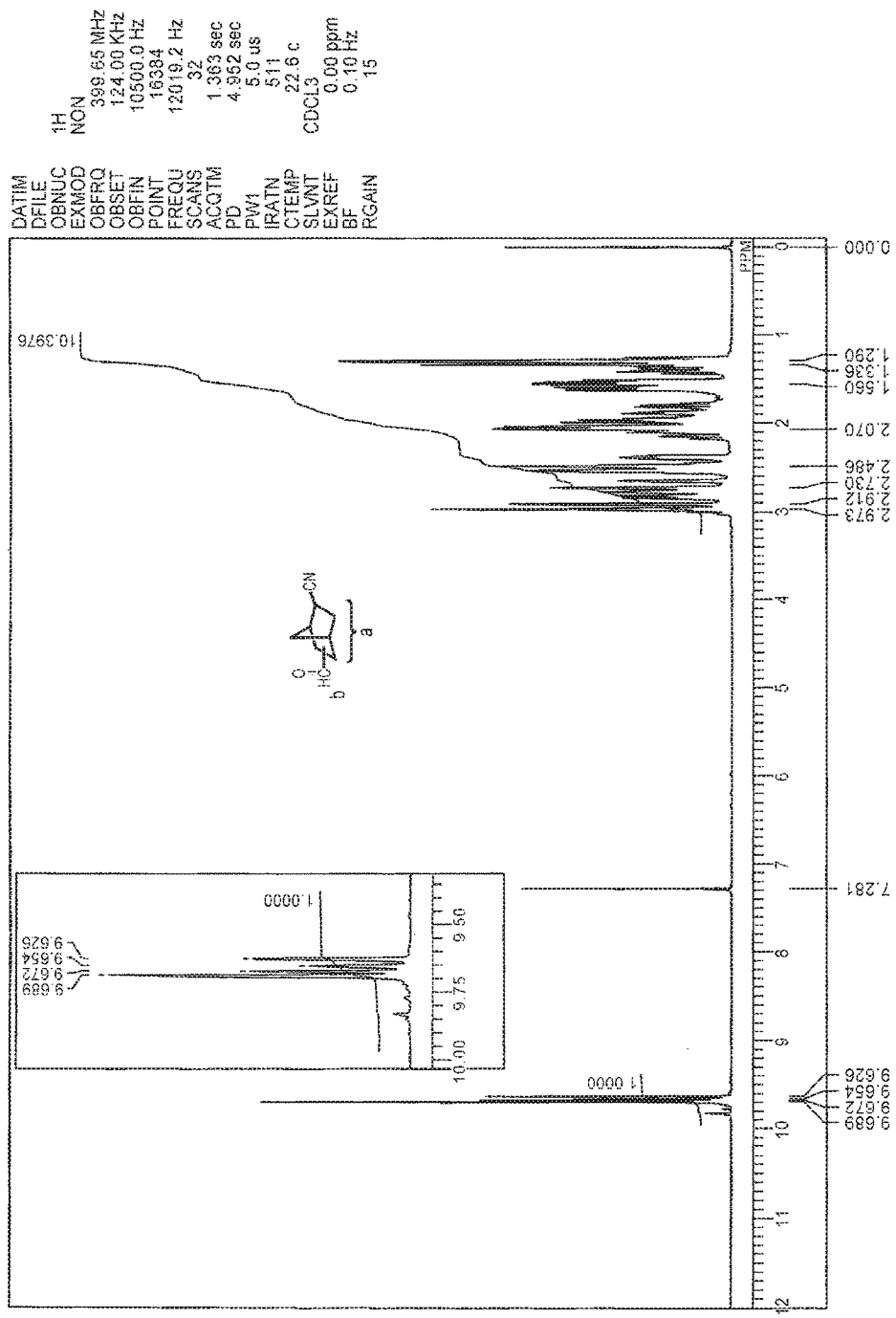
FIG. 1 is a $^1$H-NMR chart of a compound obtained in Example 1.

Hereinafter, a manufacturing method of an aldehyde compound, a manufacturing method of an amine compound, and a manufacturing method of an isocyanate compound of the present embodiment will be described in this order. Herein, a purification method of an aldehyde compound of the present embodiment will be described in the manufacturing method of an aldehyde compound.

<Manufacturing Method of Aldehyde Compound>

The manufacturing method of an aldehyde compound of the present embodiment includes a step of reacting a compound represented by the following Formula (a1) or (a2) with hydrogen and carbon monoxide in the presence of a metal compound of groups 8 to 10 and a predetermined phosphorus compound.

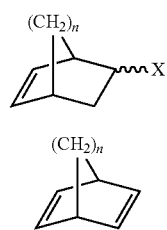

In Formula (a1), X represents a hydrogen atom, a cyano group, an aldehyde group, or a —CH=NR group, and R represents a hydrogen atom, an alkyl group having 1 to 6 carbon atoms, or an aryl group. X is preferably a cyano group or an aldehyde group, and more preferably a cyano group. In Formulae (a1) and (a2), n represents 0, 1, or 2. n is preferably 0 or 1, and more preferably 1.

The compound represented by Formula (a1) may be any of an endo-isomer and an exo-isomer, or may be a mixture containing these isomers at any ratio.

Specific examples of the compound represented by Formula (a1) include the following compounds.

(1) Examples of the compound in which n is 0 include cyclohexene, 4-cyano-1-cyclohexene, 3-cyclohexene-1-carboxyaldehyde, and 4-iminomethyl-1-cyclohexene.

(2) Examples of the compound in which n is 1 include bicyclo[2.2.1]-2-heptene, bicyclo[2.2.1]-5-heptene-2-carbonitrile, bicyclo[2.2.1]-5-heptene-2-carboxyaldehyde, and bicyclo[2.2.1]-5-hepten-2-yl methanamine.

(3) Examples of the compound in which n is 2 include bicyclo[2.2.2]-2-octene, bicyclo[2.2.2]-5-octene-2-carbonitrile, bicyclo[2.2.2]-5-octene-2-carboxyaldehyde, and bicyclo[2.2.2]-5-hepten-2-yl methanamine.

Examples of the compound represented by Formula (a2) include the following compounds.

(1) Examples of the compound in which n is 0 include 1,4-cyclohexadiene.

(2) Examples of the compound in which n is 1 include bicyclo[2.2.1]hepta-2,5-diene.

(3) Examples of the compound in which n is 2 include bicyclo[2.2.2]octa-2,5-diene.

In the present embodiment, it is preferable to use the compound represented by Formula (a1), and it is more preferable for n to be 1. Specifically, as such a compound, a compound represented by the following Formula (1) can be preferably used.

In Formula (1), X has the same definition as X in Formula (a1). X is preferably a cyano group or an aldehyde group, and more preferably a cyano group.

Herein, the compound represented by Formula (1) may be any of an endo-isomer and an exo-isomer, and may be a mixture containing these isomers at any ratio.

The metal compound of groups 8 to 10 used in the reaction of the present embodiment is a rhodium compound, a cobalt compound, a ruthenium compound, or an iron compound.

Examples of the rhodium compound include Rh(acac)(CO)$_2$, Rh(acac)$_3$, RhCl(CO)(PPh$_3$)$_2$, RhCl(PPh$_3$)$_3$, RhBr(CO)(PPh$_3$)$_2$, Rh$_2$(CO)$_8$, Rh$_4$(CO)$_{12}$, Rh$_6$(CO)$_{16}$, and the like. Examples of the cobalt compound include HCo(CO)$_3$, HCo(CO)$_4$, Co$_2$(CO)$_8$, HCo$_3$(CO)$_9$, and the like. Examples of the ruthenium compound include Ru(CO)$_3$(PPh$_3$)$_2$, RuCl$_2$(PPh$_3$)$_3$, RuCl$_3$(PPh$_3$)$_3$, Ru$_3$(CO)$_{12}$, and the like. Examples of the iron compound include Fe(CO)$_5$, Fe(CO)$_4$PPh$_3$, Fe(CO)$_4$(PPh$_3$)$_2$, and the like. Herein, "acac" means acetylacetonate.

The rhodium compound used in the reaction of the present embodiment is not particularly limited as long as it is a compound containing monovalent rhodium metal, and examples thereof include rhodium carbonyl catalysts such as dicarbonyl acetylacetonate rhodium (Rh(acac)(CO)$_2$), dodecacarbonyl tetrarhodium (Rh$_4$(CO)$_{12}$), hexadecacarbonyl hexarhodium (Rh$_6$(CO)$_{16}$), and octacarbonyl rhodium (Rh$_2$(CO)$_8$); rhodium chloride; and the like.

The phosphorus compound used in the reaction of the present invention is represented by the following Formula.

$(R^1O)_3P$

In the formula, a plurality of $R^1$s may be the same as or different from each other, and represents an alkyl group having 1 to 16 carbon atoms that may have a substituent or an aryl group having 6 to 16 carbon atoms that may have a substituent.

Examples of the substituent of the alkyl group having 1 to 16 carbon atoms or the aryl group having 6 to 16 carbon atoms include an alkyl group having 1 to 6 carbon atoms, an alkoxy group having 1 to 6 carbon atoms, an alkenyl group having 1 to 6 carbon atoms, a hydroxyl group, an amino group, a cyano group, and the like.

In the present embodiment, $R^1$ is preferably an aryl group having 6 to 16 carbon atoms that may have a substituent.

Specific examples of the phosphorus compound include trivalent phosphorus compounds such as triphenyl phosphite, trimethyl phosphite, triethyl phosphite, tripropyl phosphite, triisopropyl phosphite, trimethylphenyl phosphite, and tris(2,4-di-tert-butylphenyl)phosphite. One kind of these can be used singly, or two or more kinds thereof can be used in combination.

A hydroformylation reaction using these raw materials can be performed such that it satisfies the following condition (1), the condition (2), and/or the condition (3). In the present embodiment, it is preferable for the reaction to satisfy two conditions including the condition (1) and the condition (2).

(1) The amount of the metal of groups 8 to 10 included in the metal compound of groups 8 to 10 is 0.01 ppmmol to 300 ppmmol, preferably 0.15 ppmmol to 100 ppmmol, more preferably 0.5 ppmmol to 100 ppmmol, and particularly preferably 1 ppmmol to 100 ppmmol, with respect to 1 mol of the compound represented by Formula (a1) or (a2).

(2) A molar ratio of the phosphorus compound (mol)/the metal of groups 8 to 10 (mol) contained in the metal compound of groups 8 to 10 is equal to or greater than 100, preferably equal to or greater than 150, and more preferably equal to or greater than 200. The upper limit thereof is not particularly limited. However, from the viewpoint of the aforementioned effects, the upper limit is equal to or less than 1,000,000, preferably equal to or less than 100,000, more preferably equal to or less than 50,000, and particularly preferably equal to or less than 10,000. The lower limit and the upper limit can be combined in any way.

(3) A molar ratio of the phosphorus compound (mol)/the compound represented by Formula (a1) or (a2) (mol) is 0.003 to 0.05, preferably 0.003 to 0.03, and more preferably 0.003 to 0.02.

Herein, the range of the numerical values of the conditions (1) to (3) can be combined in any way.

The method satisfying such conditions can achieve excellent productivity of an aldehyde compound and can obtained high yield, even when the amount of the metal of groups 8 to 10 is reduced. Presumably, because the amount of the phosphorus compound used is increased, the activity of the metal compound of groups 8 to 10 is improved more than expected, hence the aforementioned effects are obtained. It is also considered that the compound represented by Formula (a1) or (a2) exerts a strong steric or electronic influence, hence the aforementioned effects are obtained.

Specifically, an aldehyde compound can be synthesized in the following manner.

First, a rhodium compound, a phosphorus compound, and the compound as a raw material represented by Formula (a1) or (a2) are put into a reactor. Then hydrogen and carbon monoxide gas are supplied into the reactor, and in this state, a hydroformylation reaction can be performed at a temperature of 30° C. to 120° C. under a pressure of 0.1 MPa to 1.0 MPa for a reaction time of 1 hour to 8 hours. Herein, a uniform reaction system including only an oil phase or a double layer reaction system including a water layer and an oil layer can be appropriately selected to perform the hydroformylation reaction.

In this way, the compound represented by Formula (a1) or (a2) is hydroformylated, and an aldehyde compound is synthesized.

The hydroformylation reaction can be performed without using a solvent, and can use a substituted or unsubstituted aromatic compound, a substituted or unsubstituted aliphatic hydrocarbon compound, or an alcohol. The hydroformylation reaction can be performed in a solvent such as toluene, benzene, hexane, octane, acetonitrile, benzonitrile, o-dichlorobenzene, ethanol, pentanol, or octanol. The hydroformylation reaction of the present embodiment exhibits excellent reactivity at a high concentration. Accordingly, the hydroformylation reaction can be performed without using a solvent. As a result, a step of evaporating a solvent and the like become unnecessary, hence the reaction is performed by a simple step. Furthermore, the volume efficiency is improved, and the production efficiency becomes excellent.

By the manufacturing method of the present embodiment, an aldehyde compound represented by the following Formula (b1) is synthesized from the compound of Formula (a1). Moreover, from the compound of Formula (a2), an aldehyde compound represented by the following Formula (b2) is synthesized.

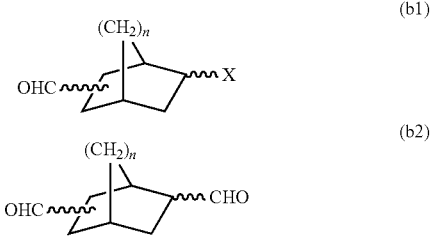

When n is 1 or 2, and X is a group other than a hydrogen atom, the compound represented by Formula (b1) or (b2) can be obtained in the form of either a "compound in which the 2-position and the 5-position have been substituted with a predetermined group (hereinafter, the compound will be referred to as a "2,5-isomer")" or a "compound in which the 2-position and the 6-position have been substituted with a predetermined group (hereinafter, the compound will be referred to as a "2,6-isomer")", or can be obtained in the form of a mixture containing these isomers at any ratio. Depending on the steric configuration of the substituent, each of the 2,5-isomer and the 2,6-isomer can be obtained in any form including an endo-endo isomer, an endo-exo-isomer, and an exo-exo-isomer, or can be obtained in the form of a mixture containing at least two kinds of these isomers at any ratio.

Herein, when n is 0, and X is a group other than a hydrogen atom, the compound represented by Formula (b1) or (b2) can be obtained in the form of either a cis-isomer or a trans-isomer, or can be obtained in the form of a mixture containing these isomers as any ratio.

In Formula (b1) or (b2), X and n have the same definition as X in Formula (a1) or (a2).

In the present embodiment, the compound represented by Formula (b1) is preferably obtained, and examples of such a compound include a compound represented by the following Formula (2).

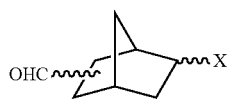

(2)

In Formula (2), X has the same definition as X in Formula (1).

Herein, the aldehyde compound represented by Formula (2) can be obtained in the form of either a "compound in which the 2-position of bicyclo[2.2.1]heptane has been substituted with the substituent X and the 5-position thereof has been substituted with an aldehyde group (hereinafter, the compound will be referred to as a "2,5-isomer")" or a "compound in which the 2-position has been substituted with the substituent X and the 6-position has been substituted with an aldehyde group (hereinafter, the compound will be referred to as a "2,6-isomer")", or can be obtained in the form of a mixture containing these isomers at any ratio. Furthermore, depending on the steric configuration of the substituent, each of the 2,5-isomer and the 2,6-isomer can be obtained in any form including an endo-endo isomer, an endo-exo-isomer, and an exo-exo-isomer, or can be obtained in the form of a mixture containing at least two kinds of these isomers at any ratio.

After the hydroformylation reaction ends, a target aldehyde compound can be obtained by performing a purification step which will be described later.

<Purification Method of Aldehyde Compound>

The purification method of an aldehyde compound of the present embodiment includes a step of neutralizing a reaction solution, which contains the aldehyde compound obtained as above, by adding water and the following base compound to the reaction solution, and a step of distilling the neutralized reaction solution.

The reaction solution which contains the aldehyde compound contains the aldehyde compound represented by the Formula (b1) or (b2), a phosphorus compound, and a compound containing rhodium. In the present embodiment, the "compound containing rhodium" also includes any of a compound in the form of a complex consisting of the rhodium compound added as a raw material, the phosphorus compound, $CO/H_2$ and a free rhodium compound.

When water and a base compound are added to the reaction solution, water and an aqueous solution of a base compound may be added, or only a solution containing a base compound may be added.

The amount of water to be mixed is 2.0% by mass to 10.0% by mass, preferably 5.0% by mass to 9.0% by mass, more preferably 6.0% by mass to 9.0% by mass, with respect to the total amount of the solution of the mixture. This is the total amount of water and water of the aqueous solution of a base compound.

In the present embodiment, the base compound used in the reaction is at least one kind selected from among carbonate and hydrogen carbonate of metals of group I on the periodic table and carbonate and hydrogen carbonate of metals of group II on the periodic table.

Examples of the base compound include sodium hydrogen carbonate, sodium carbonate, potassium hydrogen carbonate, potassium carbonate, calcium carbonate, magnesium carbonate, and the like.

Herein, at a point in time when the base compound has been added, in some cases, a reaction product (impurities) derived from the base compound and the phosphorus compound is precipitated, or alternatively, a reaction product (impurities) is precipitated similarly to the still residue remaining after distillation. Accordingly, from the viewpoint of industrial process, it is preferable to use potassium hydrogen carbonate or potassium carbonate as the base compound. If such bases containing potassium are used, the precipitation of the aforementioned reaction product (impurities) can be inhibited.

Particularly, potassium carbonate exhibits high solubility in water and makes it possible to prepare a high-concentration aqueous solution. Potassium carbonate can increase neutralization efficiency from the viewpoint described above, and availability thereof is high. Therefore, it can also be suitably used for mass production.

Specifically, purification of an aldehyde compound can be performed as below.

A mixture of a compound containing rhodium, a phosphorus compound, and a compound represented by Formula (b1) or (b2) is put into a reactor. Then water is added thereto, and the resultant is treated for a reaction time of 2 hours to 10 hours under normal pressure at a temperature of 40° C. to 80° C., preferably at 40° C. to 50° C.

Thereafter, an aqueous solution of a base compound was added thereto to perform a neutralization treatment. The conditions of the neutralization treatment can be appropriately set according to the manufacturing scale and the like. However, the neutralization treatment is preferably performed within a temperature range of equal to or higher than 40° C. and equal to or lower than 50° C. Furthermore, the pressure condition is preferably set to be a normal pressure, and the neutralization is preferably performed for a reaction time of 1 hour to 2 hours.

Moreover, in the present embodiment, after the neutralization treatment, distillation and purification are performed under a reduced pressure.

By these steps, it is possible to suitably separate a compound derived from a phosphorus compound while maintaining stability of the aldehyde compound represented by Formula (b1) or (b2). Consequentially, it is possible to obtain an aldehyde compound, from which a compound derived from a phosphorus compound has been separated and removed, while maintaining the yield of the aldehyde compound obtained by the preceding step.

In addition, in the purification step of the present embodiment, after water is added and a heating treatment is performed, an aqueous solution of a base compound is added. At this time, if the aqueous solution of a base compound is added within the aforementioned temperature range, it is possible to efficiently neutralize the reaction system without the need to excessively cool the reaction system. That is, if neutralization is performed within the aforementioned temperature range, it is possible to improve the production efficiency while maintaining stability of the aldehyde compound.

The manufacturing method of an amine compound of the present embodiment that will be described later and the manufacturing method of an isocyanate compound using an amine compound obtained by the aforementioned manufacturing method includes the purification method of an aldehyde compound as a step. Accordingly, the manufacturing methods are excellent in productivity and yield of the target compounds.

<Manufacturing Method of Amine Compound>

The manufacturing method of an amine compound of the present embodiment includes the following steps.

Step (a): a step of reacting a compound represented by the Formula (a1) or (a2) with hydrogen and carbon monoxide in the presence of a metal compound of groups 8 to 10 and a phosphorus compound Step (b): a step of reacting an aldehyde compound obtained by Step (a) with ammonia and with hydrogen in the presence of a catalyst The manufacturing method of an amine compound of the present embodiment includes the aforementioned manufacturing method of an aldehyde compound as in Step (a). Therefore, in Step (a), the productivity and yield of the aldehyde compound are excellent, and as a result, the productivity and yield of an amine compound as a target compound also become excellent.

Herein, because Step (a) is the same as the step in the "manufacturing method of an aldehyde compound", description of this step will not be repeated.

In step (b), the aldehyde compound represented by the Formula (b1) or (b2) that is obtained by Step (a) is iminated by being reacted with ammonia, and hydrogen is added thereto in the presence of a catalyst. In this way, an amine compound is synthesized.

As the catalyst, a metal catalyst such as nickel, platinum, palladium, or ruthenium, and the like can be used. When the aldehyde compound has a cyano group as a substituent, a —$CH_2$—$NH_2$ group is generated by hydrogen reduction.

In this way, in Step (b), the aldehyde group of the aldehyde compound becomes an amino group by imination, and the cyano group also becomes an amino group by hydrogen reduction. Consequentially, an amine compound represented by the following Formula (c1) having two amino groups is synthesized. Herein, when the aldehyde compound represented by Formula (b1) in which X is a hydrogen atom is used, an amine compound represented by the following Formula (c2) is synthesized.

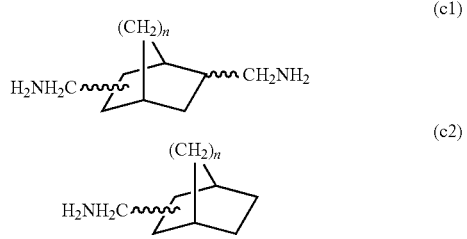

In Formula (c1) or (c2), n has the same definition as n in Formula (a1) or (a2).

When n is 1 or 2, the compound represented by Formula (c1) can be obtained in the form of either a "compound in which the 2-position and the 5-position have been substituted with a predetermined group (hereinafter, the compound will be referred to as a "2,5-isomer")" or a "compound in which the 2-position and the 6-position have been substituted with a predetermined group (hereinafter, the compound will be referred to as a "2,6-isomer")", or can be obtained in the form of a mixture containing these isomers at any ratio. Furthermore, depending on the steric configuration of the substituent, each of the 2,5-isomer and the 2,6-isomer can be obtained in any form including an endo-endo-isomer, an endo-exo-isomer, and an exo-exo-isomer, or can be obtained in the form of a mixture containing at least two kinds of these isomers at any ratio.

Herein, when n is 0, the compound represented by Formula (c1) can be obtained in the form of either a cis-isomer or a trans-isomer, or can be obtained in the form of a mixture containing these isomers as any ratio.

When n is 1 or 2, the compound represented by Formula (c2) can be obtained in the form of either an endo-isomer or an exo-isomer, or can be obtained in the form of a mixture containing these isomers at any ratio.

The compound of Formula (c1) is preferably obtained, and examples of such a compound include a compound of the following Chemical formula (3) in which n is 1.

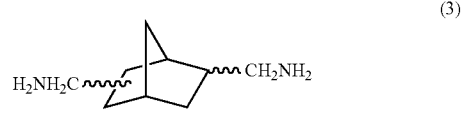

The amine compound represented by Chemical formula (3) can be obtained in the form of either a "compound in which the 2-position and the 5-position of bicyclo[2.2.1]heptane have been substituted with an aminomethyl group (hereinafter, the compound will be referred to as a "2,5-isomer")" or a "compound in which the 2-position and the 6-position have been substituted with an aminomethyl group (hereinafter, the compound will be referred to as a "2,6-isomer"), or can be obtained in the form of a mixture containing these isomers at any ratio. Furthermore, depending on the steric configuration of the substituent, each of the 2,5-isomer and the 2,6-isomer can be obtained in any form including an endo-endo-isomer, an endo-exo-isomer, and an exo-exo-isomer, or can be obtained in the form of a mixture containing at least two kinds of these isomers at any ratio.

Specifically, the aforementioned amination and hydrogenation reaction can be performed in the following manner. First, an aldehyde compound, a solvent, and a catalyst are put into a reactor, and ammonia gas is blown into the reactor. Then hydrogen is injected into the reactor at a pressure of up to about 1 MPa; the reactor is heated up to about 100° C.; and while hydrogen is being supplied into the reactor, a reaction is performed for about 1 hour to 10 hours at the aforementioned temperature and pressure. As the solvent, for example, an alcohol having 1 to 8 carbon atoms, water, or the like is suitably used.

After the reaction ends, by performing filtration of catalyst, desolvation, a purification step, and the like as in a typical case, a target amine compound can be obtained.

<Manufacturing Method of Isocyanate Compound>

The manufacturing method of an isocyanate compound of the present embodiment includes the following steps.

Step (a): a step of reacting a compound represented by the Formula (a1) or (a2) with hydrogen and carbon monoxide in the presence of a metal compound of groups 8 to 10 and a phosphorus compound Step (b): a step of reacting an aldehyde compound obtained by Step (a) with ammonia and with hydrogen in the presence of a catalyst Step (c): a step of reacting an amine compound obtained by Step (b) with a carbonylating agent The manufacturing method of an isocyanate compound of the present embodiment includes the aforementioned manufacturing method of an aldehyde compound as Step (a).

Therefore, in Step (a), the productivity and yield of the aldehyde compound are excellent, and as a result, the productivity and yield of an isocyanate compound as a target compound also become excellent.

Herein, Step (a) is the same as the step in the "manufacturing method of an aldehyde compound", and Step (b) is the same as the step in the "manufacturing method of an amine compound". Therefore, description of Step (a) and Step (b) will not be repeated.

In Step (c), the amine compound represented by Formula (c1) or (c2) obtained by Step (b) is reacted with a carbonylating agent under predetermined conditions, whereby an isocyanate compound represented by the following Formula (d1) or (d2) is synthesized. As the carbonylating agent, phosgene, a urea derivative, a carbonate derivative, carbon monoxide, or the like can be used.

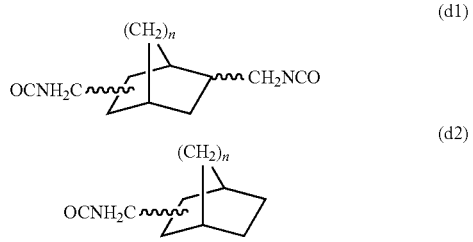

n in Formula (d1) or (d2) has the same definition as n in Formula (a1) or (a2).

When n is 1 or 2, the compound represented by Formula (d1) can be obtained in the form of either a "compound in which the 2-position and the 5-position have been substituted with a predetermined group (hereinafter, the compound will be referred to as a "2,5-isomer")" or a "compound in which the 2-position and the 6-position have been substituted with a predetermined group (hereinafter, the compound will be referred to as a "2,6-isomer")", or can be obtained in the form of a mixture containing these isomers at any ratio. Furthermore, depending on the steric configuration of the substituent, each of the 2,5-isomer and the 2,6-isomer can be obtained in any form including an endo-endo-isomer, an endo-exo-isomer, and an exo-exo-isomer, or can be obtained in the form of a mixture containing at least two kinds of these isomers at any ratio.

Herein, when n is 0, the compound represented by Formula (d1) can be obtained in the form of either a cis-isomer or a trans-isomer, or can be obtained in the form of a mixture containing these isomers at any ratio.

When n is 1 or 2, the compound represented by Formula (d2) can be obtained in the form of an endo-isomer or an exo-isomer, or can be obtained in the form of a mixture containing these isomers at any ratio.

The compound represented by Formula (d1) is preferably obtained, and examples of such a compound include a compound represented by the following Chemical formula (4) in which n is 1.

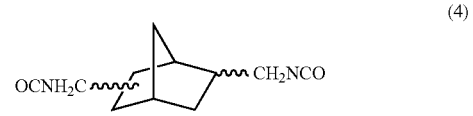

Herein, the isocyanate compound represented by Chemical formula (4) can be obtained in the form of either a "compound in which the 2-position and the 5-position of bicyclo[2.2.1]heptane have been substituted with an isocyanatomethyl group (hereinafter, the compound will be referred to as a "2,5-isomer")" or a "compound in which the 2-position and the 6-position have been substituted with an isocyanatomethyl group (hereinafter, the compound will be referred to as a "2,6-isomer")", or can be obtained in the form of a mixture containing these isomers at any ratio. Furthermore, depending on the steric configuration of the substituent, each of the 2,5-isomer and the 2,6-isomer can be obtained in any form including an endo-endo-isomer, an endo-exo-isomer, and an exo-exo-isomer, or can be obtained in the form of a mixture containing at least two kinds of these isomers at any ratio.

When phosgene is used as the carbonylating agent, specific examples of Step (c) include a method in which an amine compound and a solvent are put into a reactor first, and the amine compound is made into an amine hydrochloride by using hydrochloric acid and then reacted with phosgene; a method in which the amine compound is directly reacted with phosgene so as to obtain a carbamoyl chloride compound, and then the compound is thermally decomposed; and the like. Furthermore, after the reaction ends, by performing a purification step and the like as in a typical case, a target isocyanate compound can be obtained.

When phosgene is used as a carbonylating agent, the reaction solvent is not particularly limited. However, it is preferable to use an organic aromatic compound having a high boiling point or an ester compound that exhibits high solubility in hydrochloric acid at the time of a salt-forming reaction and exhibits high solubility in phosgene and low solubility in hydrochloric acid at the time of a phosgenation reaction. Examples of the organic aromatic compound having a high boiling point include 1,2-diethylbenzene, 1,3-diethylbenzene, 1,4-diethylbenzene, isopropylbenzene, 1,2,4-trimethylbenzene, amylbenzene, diamylbenzene, triamylbenzene, dodecylbenzene, p-cymene, cumene methylphenyl ether, ethylphenyl ether, diisoamyl ether, n-hexylether, o-dichlorobenzene, p-chlorotoluene, bromobenzene, 1,2,4-trichlorobenzene, and the like. Furthermore, the ester compound is not particularly limited, but acetic acid esters such as isoamyl acetate and isooctyl acetate are preferable. Among the solvents exemplified above, an aromatic halogen compound is particularly preferable as the solvent for embodying the present embodiment.

The isocyanate compound obtained by the present embodiment can be used as a raw material of optical materials and a coating material. Moreover, the amine compound obtained by the present embodiment can be used as a coating material and a raw material of curing agents.

EXAMPLE

Hereinafter, the present invention will be more specifically described based on examples and the like, but the scope of the present invention is not limited to the examples and the like.

Reference Example

Synthesis of bicyclo[2.2.1]-5-heptene-2-carbonitrile 195.0 g (1.40 mol) of dicyclopentadiene having purity of 95% and 163.6 (3.08 mol) of acrylonitrile to which 0.36 g (1.8 mmol) of N-nitrosodiphenylamine was added were put into a 1,000 ml autoclave. The components were reacted for 5 hours at 160° C. while being stirred and then heated to 180° C. and reacted for 2 hours, and the reaction ended. In this way, 355.6 g of a reaction liquid containing bicyclo[2.2.1]-5-heptene-2-carbonitrile was obtained. As a result analysis, it was confirmed that the reaction liquid contained 331.2 g (2.78 mol) of bicyclo[2.2.1]-5-heptene-2-carbonitrile. 352.4 g of the obtained reaction liquid containing 328.2 g (2.75 mol) of bicyclo[2.2.1]-5-heptene-2-carbonitrile was put into a 500 mL flask and subjected to distillation under reduced pressure, thereby obtaining 300.7 g (2.52 mol) of bicyclo[2.2.1]-5-heptene-2-carbonitrile as a main fraction.

Manufacture Example 1

Synthesis of 2-cyano-5-formylbicyclo[2.2.1]heptane and 2-cyano-6-formylbicyclo[2.2.1]heptane 3.7 mg (0.014 mmol) of rhodium dicarbonyl acetylacetonate, 168.73 g (1.4 mol) of bicyclo[2.2.1]-5-heptene-2-carbonitrile obtained in reference example, 4.45 g (14.3 mmol) of triphenyl phosphite, and 59.0 g of toluene were put into an electromagnetic stirring-type autoclave made of SUS316L having an internal volume of 0.5 L, and the components were stirred at 25° C., thereby obtaining 232.2 g of a liquid preparation of a Rh catalyst. Herein, conditions (1) to (3) were as follows.
 Amount of rhodium used (condition (1)): amount of rhodium contained in rhodium dicarbonyl acetylacetonate was 10 ppmmol with respect to 1 mol of bicyclo[2.2.1]-5-heptene-2-carbonitrile.
 Amount of phosphorus compound used (a) (condition (2)): triphenyl phosphite (mol)/rhodium contained in rhodium dicarbonyl acetylacetonate (mol): 1,000
 Amount of phosphorus compound (b) (condition (3)): triphenylphosphite (mol)/bicyclo[2.2.1]-5-heptene-2-carbonitrile (mol): 0.01

Thereafter, the autoclave was thoroughly purged with nitrogen and then thoroughly purged with a mixed gas of carbon monoxide/hydrogen=50/50 (volume ratio). The same gas was injected into the autoclave until the internal pressure became 0.6 MPaG, and then the autoclave was heated to 100° C. to start a hydroformylation reaction. In process of the reaction, the internal pressure of the autoclave decreases. Therefore, the mixed gas was continuously supplied such that the internal pressure was kept at 0.6 MPaG, and the liquid temperature was regulated to be kept at 80° C. In this state, the reaction was performed for 6 hours. After the reaction ended, the mixed gas in the system was purged with nitrogen, thereby obtaining 241.0 g of a reaction liquid containing 2-cyano-5,(6)-formylbicyclo[2.2.1]heptane. As a result of analyzing the reaction liquid, it was confirmed that the reaction liquid contained 208.8 g (1.4 mol) of 2-cyano-5-formylbicyclo[2.2.1]heptane and 2-cyano-6-formylbicyclo[2.2.1]heptane.

The same operation was repeated for 10 times, thereby obtaining a total of 2410.0 g of a reaction liquid containing 2088.0 g (14.0 mol) of 2-cyano-5-formylbicyclo[2.2.1]heptane and 2-cyano-6-formylbicyclo[2.2.1]heptane.

Example 1

Purification of 2-cyano-5-formylbicyclo[2.2.1]heptane and 2-cyano-6-formylbicyclo[2.2.1]heptane 263.8 g of a solution (containing 228.6 g (1.53 mol) of 2-cyano-5-formylbicyclo[2.2.1]heptane and 2-cyano-6-formylbicyclo[2.2.1]heptane) from the reaction liquid obtained in Manufacture example 1 and 14.0 g of water were put into a four-neck reaction flask having an internal volume of 2 L equipped with a reflux condenser tube, a stirring blade, and a thermometer. The components were heated to 40° C. while being stirred and then stirred for 10 hours. As a result of analyzing the obtained solution, it was confirmed that the solution contained 228.6 g (1.53 mol) of 2-cyano-5-formylbicyclo[2.2.1]heptane and 2-cyano-6-formylbicyclo[2.2.1]heptane, but triphenyl phosphite was not detected.

6.4 g (0.012 mol) of a 20% by weight of aqueous potassium hydrogen carbonate solution was added dropwise to the mixed solution within a temperature range of 40° C. to 45° C. until pH of the solution became 7.0, and the solution was stirred for 1 hour to 2 hours.

Subsequently, the solution was distilled and purified under reduced pressure, thereby obtaining 235.9 g of a solution containing 222.9 g (1.49 mol) of 2-cyano-5-formylbicyclo[2.2.1]heptane and 2-cyano-6-formylbicyclo[2.2.1]heptane (yield 97.5%). A $^1$H-NMR chart thereof is shown in FIG. 1.

After the solution was distilled under reduced pressure, the still residue was visually checked. As a result, precipitation of a salt was not observed. The results are shown in Table 1.

Examples 2 to 5 and Comparative Examples 1 to 3

An aldehyde compound was purified in the same manner as in Example 1, except that the aqueous potassium hydrogen carbonate solution used for neutralization was replaced with a 20% by weight aqueous solution of the base compound shown in Table 1. The results are shown in Table 1.

Example 6

Synthesis of 2,5-bisaminomethyl-bicyclo[2.2.1]heptane and 2,6-bisaminomethyl-bicyclo[2.2.1]heptane 89.5 g (0.6 mol) of 2-cyano-5-formylbicyclo[2.2.1]heptane and 2-cyano-6-formylbicyclo[2.2.1]heptane obtained in Example 1, 89.5 g of methanol, and 4.5 g (dry mass) of a Raney cobalt catalyst (cobalt: 94% by mass, aluminum: 3.5% by mass, manganese: 2.1% by mass) obtained by developing a cobalt-aluminum alloy containing manganese were put into an electromagnetic stirring-type autoclave made of stainless steel having an internal volume of 0.5 L, and 24.5 g (1.44 mol) of ammonia gas was blown into the autoclave.

Thereafter, the autoclave was thoroughly purged with nitrogen and then purged with hydrogen. Then hydrogen was injected into the autoclave until the internal pressure became 1.2 MPaG, and the components were heated to 100° C. while being stirred, thereby starting a reaction. In process of the reaction, the internal pressure of the autoclave decreases. Therefore, hydrogen was continuously supplied such that the pressure was kept at 1.2 MPaG, and the liquid temperature was regulated to be kept at 100° C. In this state, the hydrogenation reaction was performed for 6 hours.

The autoclave was cooled to room temperature, the Raney cobalt catalyst was removed by filtration, and then ammonia and methanol were evaporated at 60° C. and 4 kPa, thereby obtaining 102.0 g of a solution containing 2,5-bisaminomethyl-bicyclo[2.2.1]heptane and 2,6-bisaminomethyl-bicyclo[2.2.1]heptane.

102.0 g of the solution containing 2,5-bisaminomethyl-bicyclo[2.2.1]heptane and 2,6-bisaminomethyl-bicyclo

Figure 2:
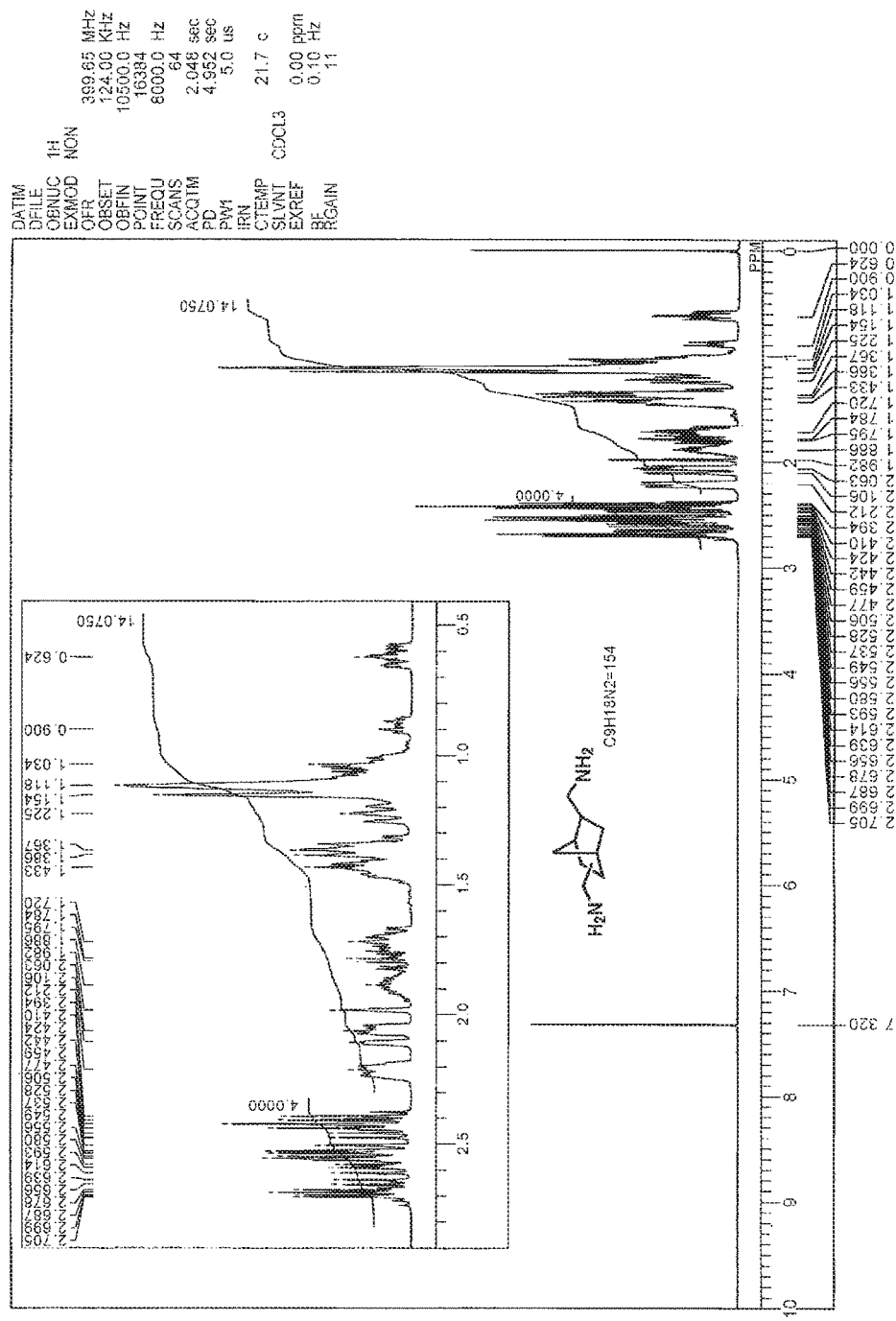
FIG. 2 is a $^1$H-NMR chart of a compound obtained in Example 6.

[2.2.1]heptane was put into a 200 ml flask, and the solution was distilled under reduced pressure, thereby obtaining 79.0 of a mixture of purified 2,5-bisaminomethyl-bicyclo[2.2.1]heptane and 2,6-bisaminomethyl-bicyclo[2.2.1]heptane. A $^1$H-NMR chart thereof is shown in FIG. 2. The same operation was repeated twice, thereby obtaining 158 g of a mixture of purified 2,5-bisaminomethyl-bicyclo[2.2.1]heptane and 2,6-bisaminomethyl-bicyclo[2.2.1]heptane.

Example 7

Figure 3:
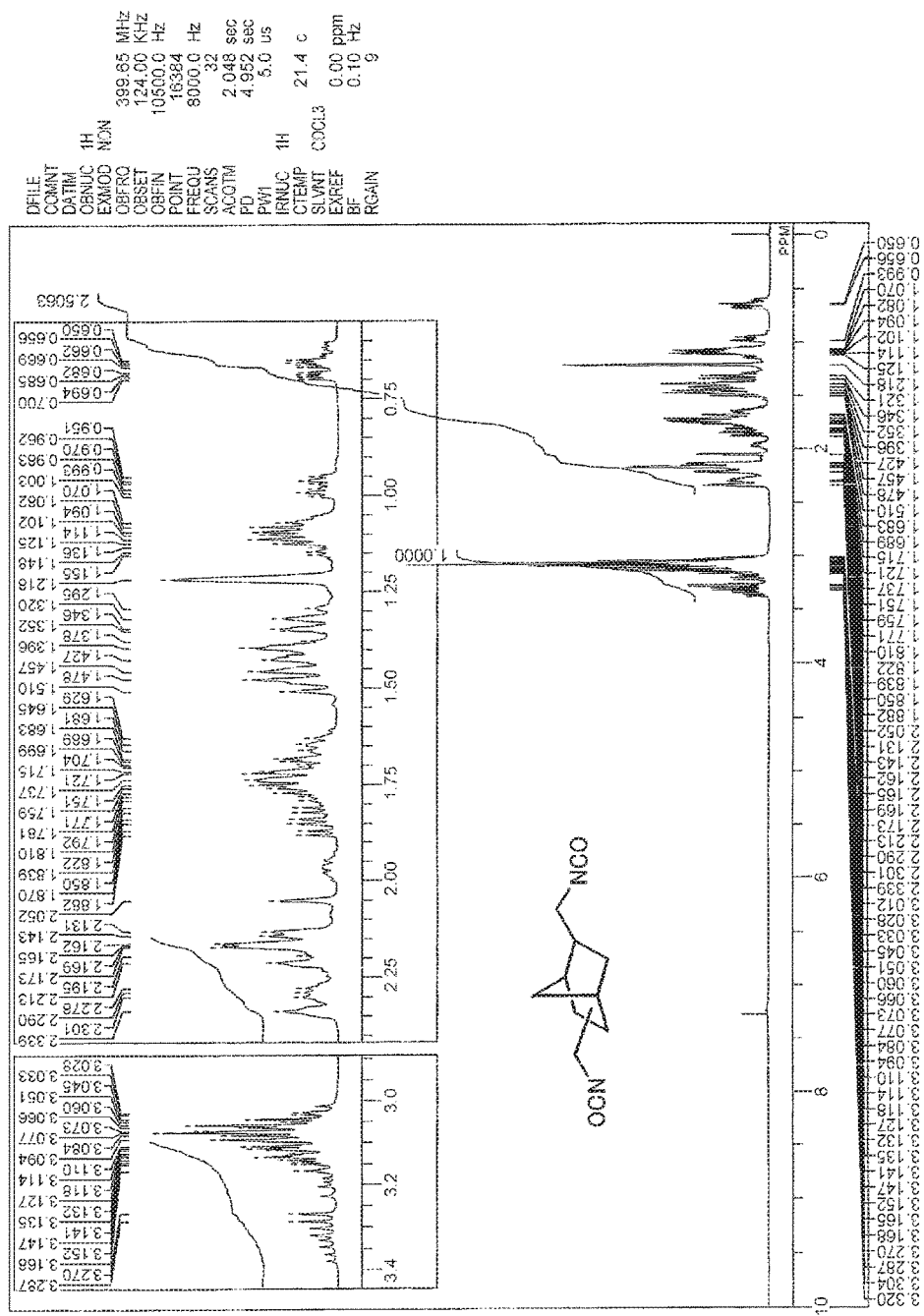
FIG. 3 is a $^1$H-NMR chart of a compound obtained in Example 7.

Synthesis of 2,5-bisisocyanatomethyl-bicyclo[2.2.1]heptane and 2,6-bisisocyanatomethyl-bicyclo[2.2.1]heptane 958 g of o-dichlorobenzene was put into a five-neck flask having an internal volume of 2 L equipped with a reflux condenser tube, a stirring blade, a thermometer, a gas blowing tube, and a raw material inlet tube. Furthermore, 154.2 g (1.0 mol) of 2,5-bisaminomethy-bicyclo[2.2.1]heptane and 2,6-bisaminomethy-bicyclo[2.2.1]heptane obtained in Example 6 and 702 g of o-dichlorobenzene were put into a raw material tank. Thereafter, the reactor was heated to 120° C. at 0.1 MPa, and then injection of hydrochloric acid gas from a hydrochloric acid blowing tube at a rate of 43.8 g/hr and injection of amine, which was diluted with a solvent in the raw material tank, from a raw material injection pump at a rate of 428.1 g/hr were started at the same time, and the entirety of the hydrochloric acid gas and amine were injected into the reaction contained over 2 hours. Furthermore, while hydrochloric acid gas was being injected at a rate of 20 g/hr, the resultant was aged for 1 hour. After the reaction ended, a reaction mass of hydrochloride was heated to 160° C., then phosgene was blown into the reactor at 100 g/hr (1.0 mol/hr) from a phosgene blowing tube, and a reaction was performed for 6 hours while maintaining the temperature. After the reaction ended, the unreacted phosgene and hydrochloric acid gas in the system were purged with nitrogen, and desolvation was performed, thereby obtaining 200.9 g of a solution containing 2,5-bisisocyanatomethyl-bicyclo[2.2.1]heptane and 2,6-bisisocyanatomethyl-bicyclo[2.2.1]heptane. Furthermore, the solution was distilled under reduced pressure, thereby obtaining 175.7 g of a mixture of 2,5-bisisocyanatomethyl-bicyclo[2.2.1]heptane and 2,6-bisisocyanatomethyl-bicyclo[2.2.1]heptane having purity of 99.0%. A $^1$H-NMR chart thereof is shown in FIG. 3.

The above examples describe the case of obtaining a mixture of a compound (2,5-isomer) in which the 2-position and the 5-position of bicyclo[2.2.1]heptane have been substituted and a compound (2,6-isomer) in which the 2-position and the 6-position have been substituted. However, depending on the reaction conditions, either the 2,5-isomer or the 2,6-isomer can be obtained. Moreover, depending on the steric configuration of the substituent, the 2,5-isomer can be obtained in any form including an endo-endo-isomer, an endo-exo-isomer, and an exo-exo isomer, or can be obtained in the form of a mixture containing at least two kinds of these isomers at any ratio. Likewise, the 2,6-isomer can be obtained in any form including an endo-endo-isomer, an endo-exo-isomer, and an exo-exo-isomer, or can be obtained in the form of a mixture containing at least two kinds of these isomers.

TABLE 1

| | Base compound | Yield of aldehyde compound: % | Precipitation of salt |
|---|---|---|---|
| Example 1 | KHCO$_3$ | 97.5 | Not occurred |
| Example 2 | K$_2$CO$_3$ | 95.7 | Not occurred |
| Example 3 | NaHCO$_3$ | 95.8 | Occurred |
| Example 4 | Na$_2$CO$_3$ | 96.6 | Occurred |
| Example 5 | CaCO$_3$ | 93.5 | Occurred |
| Comparative example 1 | NaOH | 19.9 | Occurred |
| Comparative example 2 | KOH | 25.6 | Not occurred |
| Comparative example 3 | Ca(OH)$_2$ | 36.3 | Occurred |

In Examples 1 to 5, the aldehyde compound could be obtained at high yield of equal to or greater than 90%. In contrast, in Comparative examples 1 to 3, the aldehyde compound was obtained at low yield of equal to or less than 50%. Moreover, in Examples 1 and 2, precipitation of impurities derived from the base compound and the phosphorus compound was not observed in the still residue, and it showed that the present invention is industrially useful.

The present application claims priority based on Japanese Patent Application No. 2012-247464 filed on Nov. 9, 2012, the entire content of which is incorporated herein.

The invention claimed is:
1. A manufacturing method of an isocyanate compound, comprising:
a step of obtaining a reaction solution containing an aldehyde compound by reacting a compound represented by the following Formula (a1) or (a2) with hydrogen and carbon monoxide in the presence of a metal compound of groups 8 to 10 and a phosphorus compound;
a step of neutralizing the reaction solution by adding water and a base compound to the reaction solution;
a step of purifying an aldehyde compound by distilling the neutralized reaction solution;
a step of reacting the aldehyde compound with ammonia and with hydrogen in the presence of a catalyst to obtain an amine compound; and
a step of reacting the amine compound with a carbonylating agent to obtain an isocyanate compound,
wherein the phosphorus compound is represented by the following Formula (R$^1$O)$_3$P, wherein in the formula, a plurality of R$^1$s may be the same as or different from each other, and represents an alkyl group having 1 to 16 carbon atoms that may have a substituent or an aryl group having 6 to 16 carbon atoms that may have a substituent, and
wherein the base compound is potassium hydrogen carbonate,

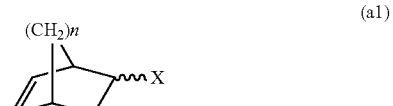

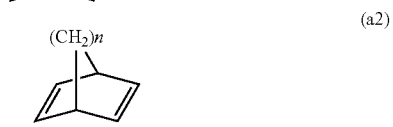

in Formula (a1), X represents a hydrogen atom, a cyano group, an aldehyde group, or a —CH=NR group; R represents a hydrogen atom, an alkyl group having 1 to 6 carbon atoms, or an aryl group; and in Formulae (a1) and (a2), n represents 0, 1, or 2,
and
wherein the step of neutralizing the reaction solution is performed within a temperature range of equal to or higher than 40° C. and equal to or lower than 50° C.

2. The manufacturing method of an isocyanate compound according to claim 1,
wherein the phosphorus compound is at least one selected from the group consisting of triphenyl phosphite, trimethyl phosphite, triethyl phosphite, tripropyl phosphite, triisopropyl phosphite, trimethylphenyl phosphite, and tris(2,4-di-tert-butylphenyl)phosphite.

3. The manufacturing method of an isocyanate compound according to claim 1,
wherein the metal compound of groups 8 to 10 is a rhodium compound, a cobalt compound, a ruthenium compound, or an iron compound.

4. The manufacturing method of an isocyanate compound according to claim 1,
wherein the metal compound of groups 8 to 10 is a rhodium compound.

5. The manufacturing method of an isocyanate compound according to claim 1,
wherein a compound represented by the Formula (a1) is used, and the compound is a compound represented by the following Formula (1),

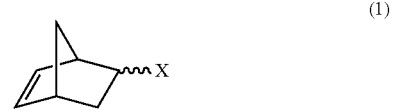

(1)

in Formula (1), X has the same definition as X in Formula (a1).

* * * * *